US005914121A

United States Patent [19]
Robey et al.

[11] Patent Number: 5,914,121
[45] Date of Patent: Jun. 22, 1999

[54] FORMATION OF HUMAN BONE IN VIVO USING CERAMIC POWDER AND HUMAN MARROW STROMAL FIBROBLASTS

[75] Inventors: Pamela Gehron Robey, Bethesda, Md.; Paolo Bianco, Rome, Italy; Sergei Kuznetsov, Bethesda, Md.; David Rowe, West Hartford, Conn.; Paul Krebsbach; Mahesh H. Mankani, both of Bethesda, Md.

[73] Assignee: The United States of America as represented by the Secretary of the Department of Health and Human Services, Washington, D.C.

[21] Appl. No.: 08/798,715

[22] Filed: Feb. 12, 1997

[51] Int. Cl.[6] .............................. A61F 2/00; A01N 63/00; A61K 9/14; C12N 5/00
[52] U.S. Cl. .......................... 424/423; 424/422; 424/426; 424/489; 424/93.7; 435/325; 435/366; 435/372; 435/395
[58] Field of Search ..................................... 435/325, 366, 435/372, 395; 424/93.7, 422, 423, 426, 489

[56] References Cited

U.S. PATENT DOCUMENTS

| | | | |
|---|---|---|---|
| 5,226,914 | 7/1993 | Caplan et al. | 623/16 |
| 5,270,300 | 12/1993 | Hunziker | 514/12 |
| 5,290,552 | 3/1994 | Sierra et al. | 424/94.64 |
| 5,354,736 | 10/1994 | Bhatnagar | 514/14 |
| 5,651,982 | 7/1997 | Marx | 424/450 |
| 5,736,160 | 4/1998 | Ringeisen et al. | 424/487 |

OTHER PUBLICATIONS

B.A. Ashton, et al., "Characterization of Cells with High Alkaline Phosphatase Activity Derived From Human Bone and Marrow: Preliminary Assessment of Their Osteogenicity", *Bone* 6:313–319 (1985).

I. Bab. et al., "Kinetics and Differentiation of Marrow Stromal Cells in Diffusion Chambers In Vivo", *J. Cell. Sci.* 84:139–151 (1986).

I. Bab, et al., "Osteogenesis in In Vivo Diffusion Chamber Cultures of Human Marrow Cells", *Bone and Mineral* 4:373–386 (1988).

Bennett, et al., "Adipocytic Cells Cultured from Marrow Have Osteogenic Potential", *Journal of Cell Science* 99:131–139 (1991).

Z. Bogdanovic, et al., "Upstream Regulatory Elements Necessary for Expression of the Rat Col1A1 Promoter in Transgenic Mice", *Journal of Bone and Mineral Research* 9(2):285–292.

E. Boynton, et al., "Human Osteoblasts Survive and Deposit New Bone When Human Bone is Implanted in SCID Mouse", *Bone* 18(4):321–326 (1996).

Chailakhyan et al., *Bull. Exper. Biol. Med.* 86:1533 (English Abstract only).

J.E. Davies, "Human Bone MarrowCells Synthesize Collagen, In Diffusion Chambers, Implanted Into the Normal Rat", *Cell Biology International Reports* 11(2):125–130 (1987).

J.E. Dennis, et al., "Osteogenesis in Marrow–Derived Mesenchymal Cell Porous Ceramic Composites Transplanted Subcutaneously: Effect of Fibronectin and Laminin on Cell Retention and Rate of Osteogenic Expression", *Cell Transplantation* 1(1):23–32 (1992).

L.W. Fisher, et al., "Purification and Partial Characterization of Small Proteoglycans I and II, Bone Sialoproteins I and II, and Osteonectin From The Mineral Compartment of Developing Human Bone", *The Journal of Biological Chemistry* 262(20):9702–9708 (1987).

A.J. Friedenstein, et al., "Bone Marrow Osteogenic Stem Cells: In Vitro Cultivation and Transplantation in Diffusion Chambers", *Cell Tissue Kinet.* 20:263–272 (1987).

A.J. Friedenstein, et al., "Osteogenic Stem Cells in the Bone Marrow", *Bone and Mineral Research* 7:243–272 (1990).

Gerasimov et al., *Bull. Exper. Biol. Med.* 101:802 (1986) (English Abstract only).

J. Goshima, et al., "The Origin of Bone Formed in Composite Grafts of Porous Calcium Phosphate Ceramic Loaded with Marrow Cells", *Clinical Orthopaedics and Related Research* 269:274–283 (1991).

R. Gundle, et al., "Human Bone Tissue Foundation in Diffusion Chamber Culture in Vivo by Bone–Derived Cells and Marrow Stromal Fibroblastic Cells", *Bone* 16(6):597–601 (1995).

S.E. Haynesworth, et al., "Characterization of Cells with Osteogenic Potential from Human Marrow", *Bone* 13:81–88 (1992).

P.H. Krebsbach. "Transgenic Expression of Col1A1–Chloramphenicol Acetyltransferase Fusion Genes in Bone: Differential Utilization of Promoter Elements in Vivo and in Cultured Cells", *Molecular and Cellular Biology* 13(9):5168–5174 (1993).

P.H. Krebsbach, "Marrow Stromal Fibroblasts Activate a Bone Specific Collagen I Construct and Form Bone In Vivo," *American Society for Bone and Mineral Research* (Sep. 1995).

Kuznetsov et al., *Bull. Exper. Biol. Med.* 108:1186 (1989) (English Abstract only).

(List continued on next page.)

*Primary Examiner*—Leon B. Lankford, Jr.
*Assistant Examiner*—Christopher R. Tate
*Attorney, Agent, or Firm*—Knobbe, Martens, Olson & Bear, LLP

[57] ABSTRACT

An in vivo model for human bone metabolism. Human marrow stromal fibroblasts are isolated, expanded in culture, combined with ceramic powder (hydroxyapatite) delivery vehicles with or without fibrin glue and implanted into a mammal. This protocol results in the formation of self-maintained human bone which supports hematopoiesis. This model system can be used to screen compounds which inhibit or stimulate bone formation. The marrow stromal fibroblast delivery vehicles can be implanted into humans to augment bone implants or to repair bone defects.

6 Claims, No Drawings

OTHER PUBLICATIONS

Kuznetsov et al., "Creation of a New Hematopoietic Microenvironment in Vivo by Cultured Marrow Stromal Fibroblasts: Comparison of Mouse and Human Models", The Hematopoietic Microenivronment (J6) 308. Taos, New Mexico, Feb. 16–22, 1996.

H.J. Mardon, et al., "Development of Osteogenic Tissue in Diffusion Chambers From Early Precursor Cells In Bone Marrow of Adult Rats" *Cell Tissue Res.* 250:157–165 (1987)

H.M. Patt. et al., "Hematopoietic Microenvironment Transfer by Stromal Fibroblasts Derived From Bone Marrow Varying in Cellularity", *Exp. Hematol.* 10(9):738–742 (1982).

D. Pavlin, et al., "Differential Utilization of Regulatory Domains within the α1(I) Collagen Promoter in Osseous and Fibroblastic Cells", *The Journal of Cell Biology* 116(1):227–236 (1992).

T. Yamamoto, et al., "In Vivo Osteogenic Activity of Isolated Human Bone Cells", *Journal of Bone and Mineral Research* 6(1):45–51 (1991).

FORMATION OF HUMAN BONE IN VIVO USING CERAMIC POWDER AND HUMAN MARROW STROMAL FIBROBLASTS

FIELD OF THE INVENTION

The present invention relates to methods and compositions which lead to the in vivo formation of complete and functional human bone which includes a functioning bone marrow organ. This human bone is formed from a composition comprising human marrow stromal fibroblasts (MSFs) in combination with a delivery vehicle. In particular, compositions capable of inducing human bone formation in vivo and methods of forming human bone, in mammals, are described. More particularly, when bone formation is being studied, as, for example, a part of a model for human disease or in drug screening protocols, the mammal in which the bone formation is carried out is an immunocompromised mammal.

BACKGROUND OF THE INVENTION

Bone marrow fragments or cell suspensions of murine, rat, guinea pig, rabbit, porcine, and canine origin form osteogenic tissue when transplanted into heterotopic sites in vivo. In closed systems such as diffusion chambers, bone marrow constituents form either bone or bone and cartilage depending on the size of the chamber. In open systems such as implantation under the kidney capsule where neovascularization can occur, bone ossicies surround a hematopoietic marrow resulting in formation of a bone marrow organ (Ashton et al., *Clin. Orthop.*, 151:294, 1980; Bab et al., *J. Cell Sci.*, 84:139, 1986; Friedenstein, *Bone Min. Res.*, 7:243, 1990). Bone marrow organs are characterized by the property of self-maintenance; that is, they provide physiological support to the hematopoietic tissue localized therein and remain vital for the lifetime of the recipient animal. In contrast, bone induced by transitional epithelium of urinary bladder, demineralized bone matrix, or isolated factors is not self-maintained in heterotopic sites without the continuous presence of an inducer.

MSFs become the predominant adherent cell type when human bone marrow is cultured in vitro. In cultures generated from single-cell suspensions of marrow, MSFs grow in colonies, each derived from a single precursor cell termed the colony forming unit fibroblast (CFU-F). In addition to their fibroblast-like morphology, MSFs share a variety of fibroblastic features but lack the basic characteristics of endothelial cells and macrophages. After extended culture, MSFs of mouse, rat, guinea pig, and rabbit origin have been reported to maintain the ability to form at least five types of connective tissue in transplantation systems, including bone, cartilage, fibrous tissue, adipose tissue and hematopoiesis-supporting reticular stroma (Ashton et al., *Clin. Orthop.*, 151:294, 1980; Gerasimov et al., *Bull Exper. Biol. Med.*, 101:802, 1986; Chailakhyan et al., *Bull. Exper. Biol. Med.*, 86:1533, 1978; Patt et al., *Exp. Hematol.*, 10:738, 1982; Friedenstein et al., *Cell Tissue Kinet.*, 20:263, 1987; Kuznetsov et al., *Bull. Exper. Biol. Med.*, 108:1186, 1989; Bennett et al., *J. Cell Sci.*, 99:131, 1991). Thus, MSF populations contain pluripotent stromal stem cells that are capable of proliferation, renewal and differentiation into several phenotypes. These stromal stem cells give rise to lineages distinct from those of hematopoietic stem cells. More mature osteoblastic cells isolated from rodent bone such as calvariae lose the stem cell properties of MSFs and lack the ability to form bone when transplanted after long term culture. After short-term culture they form bone, but not a bone marrow organ or cartilage.

MSFs have been loaded into various delivery vehicles and implanted into immunodeficient mice to study bone formation in vivo. Krebsbach et al. (*American Society for Bone and Mineral Research*, Baltimore, Md., September 1995) loaded cultured mouse MSFs into Gelfoam™ sponges, polyvinyl sponges, or block ceramic disks prior to implantation into immunodeficient mice. Bone formation was initiated within two weeks and increased with time. Only limited bone formation, if any, was also observed when human MSFs were cultured and loaded into Gelfoam™ sponges. Bone formation was far more exuberant in ceramic blocks when implanted into mice.

The osteogenic potential of human bone cells has also been studied using several experimental models. Primary bone cells derived from children occasionally formed bone and cartilage, but did not support hematopoiesis after intramuscular transplantation into cortisone-pretreated mice (Yamamoto et al., *J. Bone Min. Res.*, 6:45, 1991). When primary bone cells were transplanted within diffusion chambers, bone formation occurred only in the presence of osteogenic inducers (Davies, *Cell Biol. Intern. Rep.*, 11:125, 1987; Gundle et al., *Bone*, 16:597, 1995). When viable fragments of human bone were transplanted into immunodeficient mice pretreated with radiation, osteoblasts survived and deposited new bone upon preexisting bone fragments (Boynton et al., *Bone*, 18:321, 1996).

In contrast to rodent marrow cells, the osteogenic potential of human bone marrow cells is less well characterized. When adult human marrow cells were transplanted in diffusion chambers, only unmineralized fibrous tissue was formed; however, marrow cells from young children occasionally developed osteogenic tissue (Bab et al., *Bone Min.*, 4:373, 1988; Gundle et al., ibid). Like human bone cells, human MSFs showed no signs of osteogenesis in diffusion chambers transplanted intraperitoneally into nude mice (Ashton et al., *Bone*, 6:313, 1985; Gundle et al., ibid, Haynesworth et al., *Bone*, 13:81, 1992) unless they had been cultured in the presence of osteogenic inducers (Gundle et al., ibid).

There is a need for a method of stimulating new human bone formation in vivo. There is also a need for a model system which will allow the determination of compounds which inhibit or stimulate human bone formation and as a method for testing molecular engineering techniques. The present invention addresses these needs.

SUMMARY OF THE INVENTION

One embodiment of the present invention is a method of forming human bone in a mammal, comprising the steps of combining cultured human marrow stromal fibroblasts (MSFs) with hydroxyapatite/tricalcium phosphate (HA/TCP) powder to form a MSF-HA/TCP-loaded delivery vehicle; and implanting the loaded delivery vehicle into the mammal. The method may further comprise the step of combining the loaded delivery vehicle with fibrinogen and thrombin to form fibrin glue prior to the implanting step. Preferably, the mammal is an immunosuppressed mouse; more preferably, the mammal is a human. Advantageously, the delivery vehicle is implanted subcutaneously as a model of human bone metabolism, or in a site that is in need of bone repair.

The present invention also provides a composition for implantation into a mammal comprising human marrow stromal fibroblasts and hydroxyapatite/tricalcium phosphate (HA/TCP) powder. The composition may further comprise fibrin glue. Preferably, the fibrin glue is derived from mouse fibrinogen when implanted into a mouse. Alternatively, the fibrin glue is derived from human fibrinogen when implanted into a human. Advantageously, the marrow stromal fibroblasts are derived from an individual with a bone disorder in order to recapitulate the disease in a mouse model system.

Another embodiment of the present invention is a method of screening a compound for its effect on human bone marrow growth in vivo, comprising the steps of implanting either of the above compositions into an immunodeficient mouse; administering the compound to the mouse; and analyzing the bone arising from the implanted composition. Preferably, the delivery vehicle is subcutaneously implanted. Advantageously, the compound (potential therapeutic agent) is parenterally administered. Alternatively, the compound is orally administered.

Another embodiment of the invention is a method of providing a missing or defective protein in an individual in need thereof, comprising the steps of transfecting human MSFs with an expression vector encoding the missing or defective protein; combining the transfected MSFs with hydroxyapatite/tricalcium phosphate (HA/TCP) powder to form a MSF-HA/TCP-loaded delivery vehicle; and implanting the loaded delivery vehicle into the individual. Preferably, the vector is a plasmid. Alternatively, the vector is a viral vector. Advantageously, the transfecting step is calcium phosphate precipitation, electroporation and microinjection. The method may further comprise the step of combining said loaded delivery vehicle with fibrinogen and thrombin to form fibrin glue prior to the implanting step.

DETAILED DESCRIPTION OF THE PREFERRED EMBODIMENTS

The present invention includes a method of implanting human MSFs in vivo, in a mammal, such that the implanted MSFs form bone which actively supports hematopoiesis. In preferred embodiments, the human MSF-loaded delivery vehicles described herein are implanted into humans for therapeutic applications and into immunodeficient mice as a model for human disease or for drug screening assays. Implantation of these human MSF-loaded delivery vehicles into other mammals, preferably immunosuppressed mammals, is also contemplated. Human MSFs are isolated and expanded in culture using methods well known in the art, either in the presence or absence of the inducers dexamethasone (dex) and ascorbate monophosphate (ascP), and loaded into a delivery vehicle. Previous studies achieved in vivo osteogenesis from MSFs only when MSFs were expanded in the presence of dex and ascP prior to implantation. The present invention obviates the need for addition of such compounds because of the unexpected efficacy of the delivery vehicles. In general, the more permissive the delivery vehicle for osteogenesis, the less necessary it is to culture MSFs in the presence of osteogenesis inducers such as dex, ascP and growth factors.

Preferred delivery vehicles are hydroxyapatite/tricalcium phosphate (HA/TCP) powder, also referred to as ceramic powder, and HA/TCP held together with fibrin "glue." Although bone formation also occurred using HA/TCP blocks (block ceramics) and Collagraft™ sponges (HA/TCP combined with bovine type I collagen), these two delivery vehicles had disadvantages associated therewith. In particular, the use of ceramic blocks induced bone formation only on the exterior, not the interior, of the implant. In contrast to HA/TCP plus fibrin, Collagraft™ induced the formation of foreign body giant cells which are not part of normal human bone physiology.

The use of human fibrin is advantageous for therapeutic purposes because this material can be prepared from the patient or from an FDA certified donor and avoids the use of bovine collagen which can induce the formation of autologous antibodies. It should be noted that fibrin glue formed from fibrinogen by the action of thrombin holds the MSF-loaded ceramic particles together prior to and during implantation. However, it is important that the fibrin glue be degraded over time in the recipient animal as bone ossicles are formed because the persistence of the fibrin glue will inhibit continued growth of blood vessels in the newly formed bone. Human fibrinogen is not used in formation of MSF-loaded ceramic particles for implantation into mice because mice do not degrade human fibrin. Conversely, the use of human fibrinogen is preferable for implantation of human MSFs into humans because such fibrinogen can be easily isolated from blood of the individual undergoing implantation and will not induce an autoimmune reaction.

Block ceramics are not entirely acceptable because they do not permit cells to efficiently enter the interior leading to significantly slower bone formation. In contrast, the use of HA/TCP powder, either alone or held together with fibrin, allows faster bone formation within the center of the implant.

The present method may be used to generate an in vivo small animal model system for the study of human bone metabolism and bone disorders. This model system comprises immunodeficient mice, implanted with delivery vehicles loaded with human MSFs. Because the MSFs differentiate into human bone and hematopoiesis-supportive stroma in vivo, various compounds can be effectively screened for their ability to either inhibit or stimulate human bone growth using this animal model. Mice harboring human bone prepared as described above are administered a compound of interest followed by histological examination of the bone to determine whether enhanced formation or resorption has occurred. The compound may be administered parenterally (i.e. intravenously, intramuscularly, subcutaneously), topically or orally. If the MSFs are obtained from an individual with a genetic bone disease, the bone disease is essentially re-created in the immunodeficient mouse in which the subject MSFs are implanted. The mice can then be screened with various compounds to discover an effective therapeutic agent for the disorder.

In addition, the effect of molecular engineering can also be screened prior to utilization in humans. For example, human MSFs can be engineered to produce a missing or defective protein or peptide by transducing the cells with an expression vector encoding the protein. Because the nucleotide sequence of many such peptides and proteins are well known in the art, the skilled artisan would be able to produce an expression vector containing a protein or peptide of interest without undue experimentation. Such proteins and the disease caused by their absence or diminished presence include Factor VIII (hemophilia); glucocerebrosidase (Gaucher's disease), hexosaminidase A (Tay-Sachs), CFTR (cystic fibrosis), growth hormone (dwarfism) and adenosine deaminase (severe combined immunodeficiency syndrome). Many eukaryotic expression vectors, including plasmid and viral vectors, particularly retroviral and adenoviral vectors, are well known in the art. Cells may be transduced or infected by any method well known in the art. Such methods include calcium phosphate precipitation, electroporation, microinjection and viral infection. The engineered MSFs can be placed either in the marrow cavity or at a local subcutaneous implantation site. Thus, the MSFs expressing the desired protein are incorporated into the newly formed bone at a specific site and continuously express the missing or defective protein. One advantage of subcutaneous implantation is that the bone ossicle can be removed when desired.

The re-creation of a human genetic bone disease in the mouse model is discussed in Examples 9 and 10 relating to McCune Albright syndrome, a non-inherited genetic disease characterized by polyostotic fibrous dysplasia. In this study, the capacity of mutated stromal fibroblasts to form bone in an in vivo assay was compared to bone formed by MSFs from normal donors. The pattern of bone formation arising from McCune Albright MSFs was both qualitatively and quantitatively abnormal. The instant model can also be used to test the effect of mechanical forces such as stretching and compression on live human bone both in vivo and ex vivo. In addition MSFs can be genetically engineered to express a particular protein and reimplanted to determine the role of a protein gain of function or loss of function change.

The human MSF-loaded delivery vehicles of the invention can also be used to augment surgical implants and to repair skeletal defects. Areas of bone loss or other defects can be effectively seeded with MSFs leading to enhanced bone formation. Human MSF-loaded delivery vehicles are implanted at a site of bone loss, bone defect or surgical implant using surgical methods well known in the art.

In a preferred embodiment, MSFs are derived from human bone aspirates. In a preferred embodiment, from about $1 \times 10^5$ to $1 \times 10^8$ MSFs are loaded per 10 to 100 mg of delivery vehicle. The HA/TCP powder is washed with culture medium prior to combining with the MSF cell suspensions. After mixing, the MSFs-HA/TCP are incubated with rotation at about 37° C. for 40 to 90 minutes. In another preferred embodiment, fibrinogen is added to the MSF-loaded HA/TCP followed by thrombin. The resulting fibrin serves as a "glue" to hold the HA/TCP particles together.

In a preferred embodiment, for implantation into immunodeficient mice, between one and ten implants are used per animal. In a more preferred embodiment, between one and four implants are used per animal. The MSF-loaded delivery vehicles are implanted subcutaneously in the mice. The preferred implant location is along the dorsal surface of the mouse. For implantation into humans for repair of a bone defect or augmentation of a bone implant, between one and five MSF-loaded delivery vehicles are implanted at the defect site.

Mouse and human bone marrow were prepared as described in Example 1.

EXAMPLE 1

Preparation of Bone Marrow Suspensions

MSFs were derived from eight to 14 week old mice or transgenic mice carrying the procollagen type I-chloramphenicol acetyltransferase (CAT) constructs (Pavlin et al., *J. Cell Biol.*, 116:227, 1991) or non-transgenic control C57Bl/6 mice. Bone marrow from the femoral, tibial and humeral medullary cavities was flushed with α-modified Minimum Essential Medium (αMEM, Life Technologies, Grand Island, N.Y.). For comparative purposes, cells from mouse spleens were prepared by dissecting the spleen parenchyma and mincing the tissue. All procedures were performed in accordance to specification of an approved small animal protocol.

Normal human bone fragments were obtained from the femoral neck or ileum of patients ranging from 5 to 11 years of age (2 males and 8 females, mean age 8,5 years) undergoing corrective surgery under internal review board (IRB) approved procedures. Fragments of trabecular bone with red marrow were scraped with a steel blade into αMEM and pipetted repeatedly to release to marrow cells. Bone marrow aspirates from the iliac crests of healthy volunteers (7 males and 6 females, 25 to 53 years of age, mean age 38.7 years) were collected with informed consent, using local anesthesia. All human samples were collected in accordance with National Institutes of Health (NIH) regulations governing the use of human subjects under protocol D-0188. Aspirates were placed in ice cold αMEM with 100 U/ml sodium heparin (Fisher Scientific, Fair Lawn, N.J.), centrifuged at 1,000 rpm for 10 minutes and the cell pellet resuspended in fresh αMEM. All preparations were pipetted repeatedly to dissociate aggregated cells. Subsequently, marrow cell suspensions were passed consecutively through 16 and 20 gauge needles before culture.

Human foreskin fibroblasts were cultured in Dulbecco's Modified Eagle Medium (DMEM) containing 2 mM glutamine, 50 µg/ml streptomycin, 50 U/ml penicillin and 10% FBS (HyClone, Logan, Utah). Cells were used at the third cell passage.

EXAMPLE 2

High Density Bone Marrow Cell Culture

Cells were plated at the following densities: for mouse marrow, the entire marrow content of six bones (2 femora, 2 tibiae, 2 humera) which contained $6-8 \times 10^7$ nucleated cells; for mouse spleen, $10-20 \times 10^7$ nucleated cells; for human surgical specimens, $5 \times 10^6 - 5 \times 10^7$ nucleated cells; for human aspirates, $5 \times 10^6 - 20 \times 10^7$ nucleated cells per flask. Cells were cultured in 75 cm$^2$ culture flasks in 30 ml growth medium: αMEM, 2 mM glutamine, 100 U/ml penicillin, 100 mg/ml streptomycin sulfate and 20% preselected fetal bovine serum (FBS, Life Technologies or Atlanta Biological, Norcross, Ga.). Cells were cultured at 37° C. in an atmosphere of 100% humidity and 5% $CO_2$. Where indicated, MSFs were cultured in growth medium supplemented with $10^{-8}$ M Dex (Sigma, St. Louis, Mo.) and $10^{-4}$ M L-ascorbic acid phosphate magnesium salt n-hydrate (Wako, Osaka, Japan). Medium was replaced on day 1 for human aspirate cultures, and on day 7 and 14 for all cultures if not passaged by day 14.

The resulting adherent mouse cells were harvested using the following protocol: 1) two washes with Hanks' balanced salt solution (HBSS) (Life Technologies); 2) incubation with chondroitinase ABC (20 mU/ml, Seikagaku Corp., Tokyo, Japan) in αMEM for 25–35 min at 37° C.; 3) one wash with HBSS; 4) incubation with 1× trypsin-EDTA for 25–30 min at room temperature; 5) incubation with trypsin-EDTA for 25–30 min at 37° C.; 6) final wash with growth medium. Steps 2 and 3 were omitted for passages greater than two.

Human adherent cells were washed twice with HBSS, treated with two consecutive applications of trypsin-EDTA for 10–15 min each at room temperature, then washed with growth medium. Cold serum was added to the cells and the portions were combined, vigorously pipetted, centrifuged and resuspended in fresh growth medium. Passaged cells were plated at $2 \times 10^6$ cells per 75 cm$^2$ flask. Some human cells were cryopreserved in a freezing medium consisting of αMEM (44%), FBS (50%), penicillin (100 U/ml), streptomycin sulfate (100 mg/ml), dimethyl sulfoxide (5%, Sigma) and stored in liquid nitrogen. After 1–15 months, cells were thawed, plated and passaged once or twice before transplantation.

Morphological and cytochemical analyses were performed on the marrow stromal cell populations before transplantation. In high density cultures of mouse and human marrow cells, the adherent cells reached confluence within 12 to 14 days. In mouse cultures, several morphological cell types were evident within the complex multi-layered population including fibroblast-like cells, fat cells, macrophages and hematopoietic cells. After two passages, most cells exhibited a fibroblastic morphology which consisted of a large flattened cytoplasm and a large oval nucleus with prominent nucleoli. These cells comprised about 89% of the total adherent cell population.

Mouse cells from the 2nd and 10th passage, and human cells from the 3rd and 5th passage, were plated into two well chamber slides (VWR Scientific, West Chester, Pa.) at $5 \times 10^4$ cells per well. After 24 hours, the presence of α-naphthyl acetate esterase and acid phosphatase (Sigma kits 91-A and 387-A, respectively) was determined. The number of positive and negative cells for both enzymes was determined by counting at least 200 cells in each of five different regions of the slides. In parallel experiments, the same cell populations were analyzed by flow cytometry using forward scatter versus side scatter with a FACScan (Becton Dickinson, Mansfield, Mass.). The results are shown in Table 1. Using a FACScan with forward scatter to reflect the cell size, these cells had a relative forward scatter of 300 to 600. Cells in this fraction showed no detectable levels of a-naphthyl acetate esterase and acid phosphatase activity indicating that they were MSFs since MSFs lack these enzymes. The remaining cells showed high levels of α-naphthyl acetate esterase and acid phosphatase activity (Table 1). This smaller size fraction had a relative forward scatter of 50 to 200. These cells were round, bipolar, or stellate shaped and thus likely represented a mixture of macrophages and endothelial cells. The percentage of these cells decreased with progressive passages.

TABLE 1

| Source of MSFs | passage number | α-naphthyl acetate esterase | acid phosphatase | smaller size fraction |
|---|---|---|---|---|
| Mouse | 2 | 11.01 ± 0.40 | 11.03 ± 1.58 | 11.95 |
| Mouse | 10 | 4.77 ± 0.64 | 5.86 ± 0.76 | 2.92 |
| Human | 3 | 1.21 ± 0.49 | 1.36 ± 0.40 | 2.00 |
| Human | 5 | 1.55 ± 0.36 | 0.97 ± 0.55 | 5.27 |

The human marrow primary cultures developed as discrete MSF colonies with varying morphology. The presence of cell types other than MSFs was substantially lower in the human cultures than in the mouse cultures, and no active hematopoiesis was evident. After 3 or 5 passages, adherent human marrow cells consisted of a nearly, pure population of MSFs (Table 1).

EXAMPLE 3

Loading of Cells into Delivery Vehicles

Mouse MSFs (passage numbers 1–10, $3.0–8.5 \times 10^6$ cells), human MSFs (passage numbers 2–4, $1.5–16 \times 10^6$ cells), and human foreskin fibroblasts (passage number 3, $3 \times 10^6$ cells) were loaded into the vehicles. After centrifugation at 1,000 rpm for 10 min, cell pellets were resuspended in 30–100 μl of growth medium. The following primary transplantation vehicles were loaded with cells: Gelfoam™ (Upjohn, Kalamazoo, Mich.); polyvinyl sponges; porous collagen matrices (American Biomaterials Corp., Princeton, N.J.); poly (L-lactic acid) (Zimmer, Warsaw, Ind.); human demineralized bone matrix (DBM), particles 100–200 mm, to coarse, 1–4 mm (LifeNet Transplant Services, Virginia Beach, Va.); hydroxyapatite/tricalcium phosphate ceramics (HA/TCP), blocks or powder; Collagraft™ strip, which is a mixture of HA/TCP powder with type I bovine fibrillar collagen (Zimmer). Approximate volumes of the vehicles used for transplantation, as well as methods of loading the vehicles with cells, are described in Table 2. Cells were loaded into HA/TCP blocks by slight vacuum suction. The cell suspension was placed dropwise onto a block and fluid was drawn through the block by touching the opposite side of the block with a Pasteur pipette connected to a vacuum pump.

TABLE 2

| Vehicle | Vehicle dimensions | Method of loading vehicles with cells | Loading results |
|---|---|---|---|
| Gelfoam ™ Polyvinyl sponge Collagraft ™ Collagen matrices Poly (L-lactic acid) | 50–100 mm3 cube blocks 30–50 mm³ square sheets | The vehicles were wetted with growth medium, dried briefly between filter paper, and immediately placed into a dense cell suspension (volume was slightly less than the volume of the vehicle), cells were taken up as the vehicle expanded* | >90% cells were incorporated into the vehicle |
| Demineralized bone matrix HA/TCP powder HA/TCP powder | 25 mg of powder 40 mg of powder | Powder was washed in medium, mixed with cell suspensions, incubated with rotation* | >80% cells were incorporated into the vehicle |
| HA/TCP block | 20–30 mm³ disks | Cells were pumped into the disks by a slight vacuum suction* | not determined |

*vehicles with cells were incubated at 37° C. for 40–90 min before transplantation A secondary vehicle was used in some experiments to organize HA/TCP or fine DBM powder particles with cells attached thereto. Particles bearing cells were loaded into Gelfoam™ as described above. Alternatively, vehicle particles with adherent cells were bound together in collagen gels or fibrin clots (0.3–0.5 ml volume). The collagen gel was prepared according to the manufacturer's recommendations (Zimmer). Fibrin clots were prepared from mouse fibrinogen complex (commercially available).

Briefly, human MSFs were counted, centrifuged at 135×g for 10 min., and resuspended in growth medium so that the volume in mls was equal to the number of transplants. HA/TCP powder was aliquoted into 1.7 ml oval bottom tubes at 40 mg per tube and washed with two portions of growth medium. MSFs were mixed (in 1 ml of medium) with the HA/TCP powder followed by incubation at 37° C. for 70–100 min. with slow rotation (25 rpm). The particles containing adherent MSFs were collected after a brief centrifugation (135×g for 1 min) and the supernatant was carefully removed. Mouse fibrinogen (Sigma, 30 mg/ml in 1×PBS, 12 μl) was added to the ceramic particles and the components were slowly mixed using the smallest possible area. Mouse thrombin (Sigma, 100 U/ml in 2% $CaCl_2$, 12 μl) was added to the mixture and the components were slowly mixed using the smallest possible area. The samples were incubated for several minutes at room temperature until polymerization had occurred. The caps were closed tightly to prevent drying of the transplants which were kept on ice until transplantation. The resulting fibrin clot had the consistency of a solid gel and could be removed from the tube with forceps and placed into a recipient animal.

EXAMPLE 4

Transplantation of MSF-Loaded Delivery Vehicles

Vehicles loaded with MSFs, human foreskin fibroblasts or empty vehicles were transplanted into mouse recipients. Three different strains of immunodeficient mice (8–15 week old females) were used as subcutaneous transplant recipients: NIH-bg-nu-xidBR (beige), C.B.-17/IcrCr1-scidBR (scid) and C.B.-17/IcrCr1-scid-bgBR (scid/beige). Operations were performed under anesthesia achieved by intraperitoneal injection of 2.5% tribromoethanol (Sigma) at 0.018 ml/g of body weight. Mid-longitudinal skin incisions of about 1 cm in length were made on the dorsal surface of each mouse and subcutaneous pockets were formed by blunt dissection. A single transplant was placed into each pocket with up to four transplants per animal. The incisions were closed with surgical staples.

EXAMPLE 5

Fixation, Histological Examination and Staining of Transplants

Transplants were recovered at various time points between 2 and 19 weeks after transplantation and were fixed and partially decalcified for two days in Bouin's solution (Sigma). The transplants were then transferred to 70% ethanol until paraffin embedded. Following sectioning, sections were deparaffinized, hydrated and stained with hematoxylin and eosin.

Immunohistochemical localization of human osteonectin was performed in human MSF transplants to identify the origin of the osteogenic tissue. After deparaffinization and rehydration, the sections were incubated in 0.13% pepsin and 0.01 N HCl for 1 hour at 37° C. to reactivate the antigenicity of osteonectin. Indirect immunohistochemistry was performed using rabbit anti-human osteonectin antibody (HON; 1:100) as the primary antibody (Fisher et al., *J. Biol. Chem.*, 262:9702, 1987). goat anti-rabbit IgG (1:200, Kirkegaard and Perry, Gaithersburg, Md.) was used as the secondary antibody. Mouse vertebral bone and femoral bone of human fetus were used for negative and positive controls, respectively. As another negative control, normal rabbit serum (Vector Laboratories, Burlingame, Calif.) was used in place of the primary antibody. Anti-human osteonectin antibodies reacted with bone cells within the human MSF transplant. Intense immunostaining was found in both osteoblasts and osteocytes of the new bone, whereas no immunoreactivity above background levels was seen in the tissues surrounding the transplants. Thus, the osteogenic tissue formed by human MSF transplants was of human origin and was not formed by induced mouse cells.

To confirm the origin of the cells associated with new bone formation, and to follow the fate of the transplanted mouse MSFs, MSFs were isolated from transgenic mice carrying type I procollagen reporter genes (ColCAT) and assayed for CAT activity as described below.

EXAMPLE 6

Chloramphenicol Acetyltransferase Assay

ColCAT3.6, ColCAT2.3, and ColCAT1.7 contain 3520, 2296, and 1667 bp of the rat COL1A1 promoter, respectively (Pavlin et al., *J. Cell Biol.*, 116:227, 1991). In both ColCAT3.6 and ColCAT2.3 transgenic mice, tissues expressing high levels of type I procollagen such as bone, tendon and teeth exhibit high levels of the CAT reporter gene activity, whereas such tissues from ColCAT1.7 mice have undetectable levels of CAT activity. Thus, DNA elements between −2.3 and −1.7 kb are required for COLA1 promoter expression in bone (Bogdanovic et al., *J. Bone Min. Res.*, 9:285, 1994). When primary bone cells are isolated from transgenic calvariae and cultured in vitro, ColCAT3.6 cells retain promoter activity, while activity from ColCAT2.3 is lost, suggesting that the state of differentiation or the microenvironment of the osteoblastic cells determines which region of the promoter is utilized (Krebsbach et al., *Mol. Cell. Biol.*, 13:5168, 1993).

Transplants formed by mouse MSFs prepared from transgenic mice harboring ColCAT constructs were rinsed twice in HBSS and placed in 100 $\mu$l of extraction buffer (0.25 M Tris-HCl, pH 7.8, 0.5% Triton X-100) followed by three consecutive freeze/thaw cycles (freezing on dry ice and thawing at 37° C. for 1 min). The extracts were incubated at 65° C. for 15 min to inactivate endogenous acetylase activity. CAT activity was quantitated by a fluor diffusion assay using [$^3$H]acetyl coenzyme A (200 mCi/mmol, New England Nuclear, Boston, Mass.) at 0.1 $\mu$Ci per assay. Cell extracts were overlaid with 5 ml water-immiscible scintillation cocktail (Econofluor II, New England Nuclear). The samples were incubated at room temperature and aliquots were counted hourly. CAT activity was represented as the linear regression slope of the data plotted as cpm of product produced versus time of incubation and is expressed as cpm/transplant.

MSFs from the transgenic mice formed bone in vivo and both ColCAT3.6 and ColCAT2.3 displayed CAT activity that could be measured in the newly formed bone within Gelfoam™ sponges, polyvinyl sponges and HA/TCP blocks. CAT activity in 28 day transplants was 6762±1302 and 2492±337 cpm per transplant for ColCAT3.6 and ColCAT2.3, respectively. These findings contrast the observed promoter activity in primary cultures of MSFs where CAT activity from both ColCAT3.6 and ColCAT2.3 was less than 35 cpm/h/$\mu$g protein. This indicates that transgenic-derived MSFs populate the vehicle, differentiate in vivo and reconstitute the activity of the 3.6 and 2.3 kb collagen I promoters. The donor origin of new bone in MSF heterotopic transplants is further supported by the absence of osteogenesis in the transplants of empty vehicles or of those transplanted with mouse spleen fibroblasts, human foreskin fibroblasts and in transplants of mouse MSFs into allogenic immunocompetent recipient mice. Taken together, these data suggest that in MSF transplants, new bone tissue sustains its donor origin and does not undergo substitution by bone tissue of recipient origin.

EXAMPLE 7

The ability of different vehicles to support bone formation by mouse and human MSFs is summarized in Table 3.

TABLE 3

| Transplantation Vehicle | | Source of MSFs | | |
|---|---|---|---|---|
| Primary vehicle | Secondary vehicle | Mouse | Human (Dex + AscP) | Human (w/o Dex/AscP) |
| Gelfoam ™ | | 21/23 | 5/28 | 0/30 |
| Polyvinyl sponge | | 3/5 | 0/3 | nd |
| Collagen matrix | | 2/2 | nd | nd |
| HA/TCP block | | 10/10 | 13/14 | 3/3 |
| Poly(L-lactic acid) | | | 0/2 | 0/2 |
| DBM | | | 0/3 | nd |
| DBM | Gelfoam ™ | | 0/9 | 0/8 |
| DBM | Fibrin clot | | 0/15 | nd |
| HA/TCP powder | | | 13/15 | 10/10 |
| HA/TCP powder | Gelfoam ™ | | 2/4 | 0/2 |
| HA/TCP powder | Fibrin clot | | 4/4 | nd |
| HA/TCP powder | Collagen gel | | 0/6 | nd |
| Collagraft ™ | | | 20/23 | 10/10 |

Values represent the number of transplants with new bone formation/total number of transplants. MSFs were cultured in growth medium in the presence or absence of Dex and AscP. nd - not determined.

Mouse MSF transplants in Gelfoam™ sponges formed new bone as early as two weeks after transplantation. The newly formed bone marrow organ consisted of a cortical-like structure surrounding an area of active hematopoiesis. Hematopoiesis was determined by plating mononuclear cells from the transplants in duplicate at $1 \times 10^5$ cells per ml murine methylcellulose medium (Terry Fox Laboratories, Vancouver, Canada) supplemented with 5% spleen conditioned medium, 3 U/ml human erythropoietin, 50 ng/ml human IL-6 and 100 ng/ml rat stem cell factor (Amgen, Thousand Oaks, Calif.). Colonies were counted at day 14.

The bone exhibited lacunae containing osteocytes as well as osteoblastic layers on both the inner and outer surfaces. Isolated osteoclasts were occasionally found adjacent to the bone. Inside the bony capsule, between bone trabeculae and portions of vehicle undergoing resorption, bone marrow tissue which included blood vessels and sinuses, reticular and fat stroma, and hematopoietic cells of all lineages and stages of maturation was observed. With continued growth, the bone capsule became thicker and the hematopoietic tissue more abundant. No signs of degeneration were observed in the heterotopic bone marrow organs for at least 14 weeks after transplantation. In 4 separate transplants recovered after 44 days, smears of the hematopoietic elements showed normal maturation with megakaryocytes. Methylcellulose cultures counted at day 14 revealed $179.6 \pm 15.0$ colonies per $10^5$ cells. These colony numbers are equivalent to those seen when plating mononuclear cells from skeletal murine marrow under the same conditions.

Transplants of mouse MSFs in polyvinyl sponges and collagen matrices were similar in appearance to transplants in Gelfoam™ sponges. These transplants consisted of a thin capsule of cortical bone surrounding a cavity with bone trabeculae, vehicle remnants, blood vessels, fat cells and hematopoietic tissue. However, the thickness of the cortices as well as the level of hematopoiesis was not as pronounced as in Gelfoam™ vehicles.

Two weeks after transplantation of mouse MSFs in HA/TCP blocks, newly formed bone was observed in vehicle pores at the periphery of the transplants. most of the internal pores contained fibrous tissue and vascular structures. After 4–5 weeks, many pores were filled with woven bone which was deposited against the vehicle walls. New bone showed osteocytes embedded within the matrix and a prominent osteoblastic layer was evident on lumenal surfaces. After 6–10 weeks, transplants showed areas of vehicle resorption and bone remodeling. The bone trabeculae began to merge on the periphery of the transplants, forming an incomplete bony capsule. Larger pores were layered with lamellar-like bone surrounding reticular and fat stroma with abundant hematopoietic tissue.

No obvious correlations were observed between the rate or the extent of bone formation with the number of transplanted MSFs (ranging from 3.0 to $8.5 \times 10^6$ cells per Gelfoam™ vehicle). MSFs from in vitro passages 1 to 10 were capable of bone formation. In one experiment, MSFs from the 13th passage ceased to proliferate in vitro and failed to form bone in vivo. The presence of Dex and AscP in the growth medium did not influence the rate and extent of bone formation, or the abundance and morphological appearance of hematopoietic tissue. MSFs of both transgenic mice and non-transgenic C57Bl/6 mice were capable of bone formation in both beige and scid immunodeficient recipient mice.

Bone formation was not observed in any control experiment which consisted of vehicles without cells. After several weeks in vivo, control transplants showed areas of soft connective tissue ingrowth, vehicle resorption and connective tissue encapsulation. Abundant growth of fibrous tissue with no bone formation was observed in Gelfoam™ transplants of mouse spleen fibroblasts at 4 to 10 weeks. When mouse MSFs were transplanted into allogenic immunocompetent recipients, osteogenesis was not observed.

Between $1.5 \times 10^6$ and $1.6 \times 10^7$ human MSFs were transplanted within Gelfoam™ sponges. After 3 to 11 weeks, many transplants had been resorbed and the majority of the remaining transplants contained fibrous tissue. However, bone was formed in a few transplants by human MSFs which had been cultured in the presence of Dex and AscP (Table 3). In those Gelfoam™ transplants that did form bone, a single trabecula of woven bone with no signs of remodeling was observed. The bone ossicle contained embedded osteocytes and was surrounded by a non-continuous osteoblastic layer, but had no cavity and no hematopoietic tissue.

Human MSFs within HA/TCP-containing vehicles formed bone regardless of whether the cells had been cultured in the presence or absence of Dex and AscP (Table 3). In HA/TCP blocks containing human MSFs, bone was formed in all but one transplant (Table 3). At early stages (4 to 5 weeks), bone was found in several peripheral pores, deposited against the walls of the vehicle with and osteoblastic layer lining the lumenal surface and osteocytes embedded within lacunae. After 6 to 10 weeks, the transplants showed areas of vehicle resorption, and the new bone acquired a more lamellar-like structure. Bone foci were larger and tended to merge, forming an incomplete capsule near the transplant surface.

Osteogenesis was observed in both HA/TCP powder and Collagraft™ strips (Table 3) and was more extensive than in HA/TCP blocks. However, Collagraft™ strips induced the formation of foreign body giant cells which are not part of normal human bone physiology. By 4 to 6 weeks, numerous bone trabeculae with embedded osteocytes and prominent osteoblastic layers surrounded the vehicle particles. The new bone formed networks of interconnecting trabecular structures with the intratrabecular space filled with fibrous tissue. After 8 to 10 weeks, the transplants contained an extensive network of bone. Degeneration was not detected in transplants of at least 19 weeks.

Although mouse MSFs formed bone within all vehicles tested, consistent bone formation by human MSFs was achieved only within HA/TCP blocks, HA/TCP powder and Collagraft™ strips. HA/TCP powder, Collagraft™ or powder held together with fibrin were easier to load and supported more extensive osteogenesis than HA/TCP blocks. For human therapeutic use, fibrin is advantageous because it is a human protein compared to Collagraft™ which contains bovine collagen. When Gelfoam™ was used as the primary vehicle, only a small number of human MSF transplants developed bone. No bone formation was observed with polyvinyl sponges, poly(L-lactic acid) and human DBM. Thus, HA/TCP supports the ability of human MSFs to form bone in vivo. MSFs expanded in vitro may already be committed to osteogenic differentiation and the underlying mechanism may be "permissive" rather than inductive.

No bone formation was observed in transplants of human foreskin fibroblasts in either HA/TCP powder or Collagraft™ strips. In these control transplants fixed at 3 to 8 weeks, only fibrous tissue was observed. An additional control consisting of transplants of empty HA/TCP powder and Collagraft strip vehicles also showed only fibrous tissue growth.

In many transplants of human MSFs in HA/TCP containing vehicles, areas of hematopoietic tissue were observed. The extent of the hematopoietic tissue was usually dependent on the degree of bone formation. The hematopoietic cells were always closely associated with newly formed bone. These cells consisted of predominantly mature granulocytes, although some hematopoietic precursors may have been present. The architecture of the ceramic vehicles precluded recovery of sufficient hematopoietic cell numbers for further characterization.

To further study the effect of Dex and AscP treatment of MSFs, the rate of proliferation of cells plated at low density in the presence or absence of Dex and AscP was studied in vitro. Low density human marrow cell cultures were prepared as follows.

EXAMPLE 8

Low Density Human Marrow Cell Cultures

Single bone marrow cell suspensions were prepared from human surgical specimens by passing cells through needles of decreasing diameter (16, 20 and 23 gauges) and subsequent filtration through a cell strainer 2350 (Becton Dickinson) to eliminate cell aggregates. Nucleated cells were plated at a density of $2 \times 10^4$ cells/cm$^2$. Two types of low density cultures were used. In total cultures, the entire population (adherent and non-adherent) of plated marrow cells was left undisturbed until the time of harvest. To produce cultures of adherent cells only, cells were incubated for 2.5 hours at 37° C. Subsequently, unattached cells were aspirated and cultures were washed vigorously 4 times with DMEM (Biofluids). The total and adherent cultures were used to determine if Dex and AscP directly affected the adherent stromal cell population or if the effect was mediated through the non-adherent population. Cells were cultured in the presence or absence of Dex and AscP. Half of the cultures were fixed on day 12 with methanol and stained with methyl violet (Sigma). MSF colonies of at least 50 cells were counted using a dissecting microscope, and colony forming efficiency (number of colonies per $1 \times 10^5$ marrow cells plated) was determined. On day 14, the remaining cultures were washed twice with HBSS, harvested with trypsin-EDTA and cell numbers were determined (Coulter Electronics, Hialeah, Fla.). Analysis of variance was performed and post test comparison was completed using the Bonferroni multiple comparison test.

At low initial density plating, human MSFs grew as discrete colonies, with only a few macrophages apparent throughout the cultures. The combined action of Dex and AscP did not change human MSF colony forming efficiency. However, the total cell number at the end of the culture period was elevated in the presence of Dex and AscP indicating an increase in the number of MSFs per colony (FIG. 1). This increase was statistically significant not only in total cultures (adherent and non-adherent cells), but also in adherent cultures (non-adherent cells removed after 2.5 hours) indicating a direct effect on MSFs rather than an effect mediated by the non-adherent population.

Human MSFs did not form bone when transplanted with human demineralized bone matrix (DBM). The transplants typically consisted of non-vital DBM particles surrounded by fibrous tissue. Likewise, only fibrous tissue was observed in transplants of MSFs within polyvinyl sponges and poly (L-lactic acid) vehicles (Table 3). The results of the human MSF transplantation studies revealed no obvious difference based on numbers of MSFs transplanted per vehicle, on strain of immunodeficient mouse recipients (beige, scid or beige/scid), or whether fresh or previously frozen MSFs were used. The source of bone marrow (surgical specimen versus marrow aspirate, donor age and sex) had no obvious influence on bone formation (Table 4).

TABLE 4

| Transplantation Vehicle | | Source of human MSFs | | | |
|---|---|---|---|---|---|
| | | Surgical specimens | | Aspirates | |
| Primary vehicle | Secondary vehicle | Males | Females | Males | Females |
| Gelfoam ™ | | 1/9 | 2/22 | 2/27 | |
| Polyvinyl sponge | | | | 0/3 | |
| Poly(L-lactic acid) | | | | | 0/4 |
| DBM | | | | | 0/3 |
| DBM | Gelfoam ™ | | | 0/5 | 0/12 |
| DBM | Fibrin clot | | | 0/3 | 0/12 |
| HA/TCP block | | | 3/3 | 5/6 | 8/8 |
| HA/TCP powder | | 4/4 | 8/8 | 3/3 | 8/10 |
| HA/TCP powder | Gelfoam ™ | | | 2/6 | |
| HA/TCP powder | Fibrin clot | | | 2/2 | 2/2 |
| HA/TCP powder | Collagen gel | | 0/2 | | 0/4 |
| Collagraft ™ | | 4/4 | 8/8 | 3/3 | 15/18 |

Values represent the number of transplants with new bone formation/total number of transplants. MSFs were obtained from normal bone fragments of 10 patients undergoing corrective surgery (2 males and 8 females, mean age 8.5 years) and from bone marrow aspirates of 13 normal volunteers (7 males and 6 females, mean age 38.7 years).

A number of variables had no effect on bone formation in the transplants of mouse and human MSFs. In mouse, the marrow origin (C57Bl/6 versus non-inbred mice), the presence of Dex and AscP in culture medium, the number of in vitro passages before transplantation, the number of MSFs loaded per vehicle, the nature of the transplantation vehicle or the phenotype of the immunodeficient mice had no influence on bone formation. The factors that did not influence osteogenesis by human MSFs included the marrow origin (age and sex of donor, skeletal location of excised bone, method of marrow preparation), the number of in vitro passages before transplantation, the freezing of MSFs, the number of MSFs loaded per vehicle or the phenotype of the immunodeficient recipient mice. Because the number of in vitro passages was not a critical factor, this indicates that a sufficient number of MSFs maintain their osteogenic and proliferative properties throughout the in vitro culture period examined.

EXAMPLE 9

Re-Creation of McCune-Albright Syndrome in Mice

Polyostic fibrous dysplasia is a cardinal feature of McCune-Albright syndrome, a non-inherited genetic disease resulting from activating missense mutations of the gene encoding the α subunit of the stimulatory G protein, $G_S$. To more clearly define the molecular pathway linking excess activation of the adenylyl cyclase-dependent signal transduction pathway to abnormal bone formation, and to develop an in vivo model of human bone disease, MSFs were isolated from both apparently normal and lesional tissue from affected patients. Using these cell populations, the capacity of mutated MSFs to form bone was compared to bone formed by MSFs from normal donors as described in the following examples.

EXAMPLE 10

Patients and Tissues

A total of three cases of McCune-Albright syndrome (MAS) were the subject of this study and were collected as part of an NIH protocol (Protocol 96-DK-0054). A summary of relevant clinical data is shown in Table 5. Fresh surgical specimens of bone lesions were obtained from three patients (one of which provided two different samples on two different occasions) who underwent corrective surgery under NIH IRB protocol #96-DK-0054. Samples from these specimens were used both for histology (paraffin and glycol methacrylate embedded) and for establishing cultures of marrow stromal fibroblasts. Marrow stromal fibroblasts and trabecular bone cells were isolated and cultured as described below.

TABLE 5

| Patient | Age | Sex | Site |
|---------|-----|-----|------|
| MAS M   | 8   | M   | femur |
| MAS C-2 | 12  | F   | max-fac |
| MAS F   | 25  | M   | cranial |

EXAMPLE 11

Isolation and Culture of Cells

Marrow fragments from normal and affected bone from all three patients were scraped with a steel blade and repeatedly pipetted to release cells into nutrient medium consisting of αMEM plus 20% FBS. The cell suspension was passed serially through 16 and 20 gauge needles and finally through a 70 mm cell sieve. The resulting single cell suspension was plated into 75 cm$^2$ flasks or 150 mm petri dishes at the following cell densities: for multi-colony strains, 0.67–6.7×10$^4$ /cm$^2$; for single-colony derived strains, 0.0067 to 0.067×10$^4$ /cm$^2$. Cells were cultured at 37° C. in an atmosphere of 100% humidity and 5% $CO_2$. Medium was replaced on day 7 and 14, if not passaged by day 14. For multi-colony derived strains, first passage was performed on day 9 to 12. The adherent cells were washed twice with HBSS, treated with two consecutive portions of 1×trypsin-EDTA for 10–15 min. each at room temperature and washed with growth medium. To each portion, ice-cold growth medium was added, the portions were combined, vigorously pipetted and the cells plated into 75 cm$^2$ or 175 cm$^2$ flasks at 1–2×10$^4$ cells per cm$^2$. The medium was replaced the next day. The next passages were performed in the same way when cells approached confluence.

For single-colony derived strains, first passage was performed on day 13 to 17. Individual, well separated colonies were chosen and washed with HBSS. Cloning cylinders were glued with S/PTM High Vacuum Grease (Baxter, McGaw Park, Ill.) so each surrounded the individual colony. Cells inside the cylinder were treated with two consecutive portions of 1×trypsin-EDTA for 5–10 min. each at room temperature. Released cells were transferred to individual wells of six-well plates in growth medium. The medium was replaced on the next day. Prepared single-colony derived strains were passaged again upon reaching subconfluence, usually 5 to 10 days after the first passage.

Cells were incubated with HA/TCP powder, implanted subcutaneously in the back of immunosuppressed mice, harvested between 42 and 56 days after surgery and subjected to histological analysis as described in Examples 3, 4 and 5. Prominent formation of bone was observed in implants of carriers loaded with normal MSFs. Hematopoietic tissue was also clearly established in the spaces separating the newly-formed "trabeculae". Adipocytes within hematopoietic areas were also clearly identified.

Multicolony derived MSF grown from MAS patients were expanded in culture with or without dex/ascP. Although distinct areas of bone formation indistinguishable from controls were occasionally observed in implants of MAS-derived MSFs that had been expanded in culture in the absence of dex, the dominant feature was severely reduced bone formation activity over most of the implant volume. The profile of the carrier particles were mostly lined by an inconspicuous, extremely thin layer of bone-like matrix. Cells associated with this matrix appeared not to line up as osteoblasts usually do, and were mostly oriented perpendicular to the forming surface, a pattern reminiscent of the bone formation sites seen in native fibrous dysplasia lesions. In implants of MAS-derived MSFs that were expanded in culture in the presence of dex, no bone formation was observed. The surface of the carrier was lined by a distinct layer of cells otherwise similar to those seen in implants of non-dex-treated MSFs.

This study represents the first use of implants of osteogenic precursor cells to model a genetic (human) bone disease, and provides a tool for assessing the effects of manipulation of affected cells while envisioning and developing cell, gene or drug-based therapeutic strategies.

It should be noted that the present invention is not limited to only those embodiments described in the Detailed Description. Any embodiment which retains the spirit of the present invention should be considered to be within its scope. However, the invention is only limited by the scope of the following claims.

What is claimed is:

1. A composition for implantation into a mammal, comprising human marrow stromal fibroblasts and hydroxyapatite/tricalcium phosphate (HA/TCP) powder in amounts effective to form human bone when implanted into a mammal.

2. The composition of claim 1, further comprising fibrin glue in amounts effective to form human bone when implanted into a mammal.

3. The composition of claim 2, wherein said fibrin glue is derived from mouse fibrinogen for implantation into mice.

4. The composition of claim 2, wherein said fibrin glue is derived from human fibrinogen for use in humans.

5. The composition of claim 1, wherein said marrow stromal fibroblasts are derived from an individual with a bone disorder.

6. The composition of claim 2, wherein said marrow stromal fibroblasts are derived from an individual with a bone disorder.

* * * * *